United States Patent [19]

Nguyen

[11] Patent Number: 5,110,803
[45] Date of Patent: May 5, 1992

[54] PLANT POLYSACCHARIDE FRACTIONS INDUCING PROLACTIN IN MAMMALS

[75] Inventor: Tan H. Nguyen, Saint Avé, France

[73] Assignee: Guyomarc'h Nutrition Animale, Saint-Nolff, France

[21] Appl. No.: 551,492

[22] Filed: Aug. 7, 1990

Related U.S. Application Data

[62] Division of Ser. No. 216,806, Jul. 8, 1988, Pat. No. 4,948,785.

[30] Foreign Application Priority Data

Jul. 10, 1987 [FR] France .................. 87 09857

[51] Int. Cl.$^5$ .................. A61K 31/715; C08B 37/00
[52] U.S. Cl. .................. 514/54; 536/123; 426/809
[58] Field of Search .................. 536/123, 124, 122; 514/782, 783, 775, 54; 426/807

[56] References Cited

U.S. PATENT DOCUMENTS 4,511,559  4/1985  Szendrei et al. .................. 514/54

OTHER PUBLICATIONS

Buchala et al. (1981) Carbohydrate Research vol. 89, pp. 137–143.
Hawkins et al. (1985) J. Dairy Science vol. 68, pp. 2608–2614.
Rosengarten, Jr. (1982) Journal of Ethnopharmacology, vol. 5, pp. 91–112.
Lehninger, Albert L. Biochemistry: The Molecular Basis of Cell Structure and Function, (Worth Publishers: New York, 1975), pp. 250–251.

Primary Examiner—Johnnie R. Brown
Assistant Examiner—Gary L. Kunz
Attorney, Agent, or Firm—Dressler, Goldsmith, Shore, Sutker & Milnamow, Ltd.

[57] ABSTRACT

The invention relates to a polysaccharide product containing units corresponding to rhamnose, arabinose, xylose, mannose, galactose and glucose and providing, in addition, humans and animals with an increased level of plasma prolactin when administered in an effective amount, orally or by injection. The product is substantially soluble in water and substantially insoluble in ethanol and is derived from plants of the genus Gossypium sp. of the family of the Malvaceae. The molecular mass of the polysaccharide product is generally between about $10^4$ and $10^6$ daltons and preferably between $2.20^4$ and $10^5$ daltons.

3 Claims, No Drawings

PLANT POLYSACCHARIDE FRACTIONS INDUCING PROLACTIN IN MAMMALS

This is a division of application Ser. No. 07/216,806, filed Jul. 8, 1988, now U.S. Pat. No. 4,948,785.

The subject of the present invention is polysaccharide extracts, in particular from plants, as well as procedures for extracting them and their use as medicines and food additives.

These novel polysaccharide substances have the property of increasing the secretion of prolactin, the principal hormone of lactation, and of increasing the secretion of beta-casein, the principal protein of milk, and, as a consequence, they increase the secretion of milk in women and in animals and are thus likely to find industrial applications, in particular in the nursing of infants and in the breeding of animals.

More particularly the present invention relates to polysaccharides containing units corresponding to rhamnose, arabinose, xylose, mannose, galactose and glucose and providing humans and animals with an increased level of plasma prolactin.

Furthermore, these polysaccharides are characterized in that their molecular mass lies between $10^4$ and $10^6$ daltons, and usually lies between $2 \times 10^4$ and $10^5$ daltons.

In addition, these polysaccharides contain nitrogen and sulfur, usually from 1 to 8% of nitrogen and from 0.8 to 2% of sulfur.

These products are usually of plant origin but it is possible to envisage their synthesis or semi-synthesis starting from products of diverse origin or even a total synthesis starting from known chemical compounds.

The invention also relates to procedures for the preparation of these polysaccharides from plants containing these polysaccharides by extraction with hot water, the polysaccharides being recovered from the aqueous extract obtained, which can itself be purified if necessary.

The purification can be performed by all of the known procedures but, in particular, it is possible to envisage a precipitation from the aqueous extract with the aid of organic solvents which are miscible with water and which do not dissolve the polysaccharides, in particular hydroxylated solvents such as ethanol and methanol.

It is of course possible to contemplate other methods of purification such as fractionation by molecular weight.

The products according to the present invention are extracted more especially from plants of the genus Gossypium sp. of the family of the Malvaceae and from the species *Euphorbia Hirta* Linne of the family of the Euphorbiaceae.

The procedure of the invention consists essentially in treating the organs of the plants of Gossypium sp. in particular the seeds reduced to powder and the seed cakes derived from them. In the case of *Euphorbia Hirta* it is the whole plant which is reduced to powder. The powder, which may or may not be defatted beforehand, is extracted without water to give an aqueous solution. The aqueous solution is concentrated and treated in different ways.

The concentrated aqueous solution is either lyophilized or converted into a dry powder by physical methods of evaporation and drying.

The powder thus obtained is then treated either with ethanol or with methanol or with other organic solvents which do not dissolve the polysaccharides.

The aqueous solution of total extracts may also be treated with ethanol or other solvents in order to precipitate the total polysaccharides.

Termination of the operations already mentioned yields all of the galactagogue polysaccharide fractions. If necessary, a more elaborate purification can be performed by known physical, chemical or physicochemical methods of fractionation: ultrafiltration, filtration through gel, differential precipitation, affinity chromatography, for example.

The present invention relates more particularly to the total polysaccharide extracts as well as to highly active polysaccharide fractions extracted from the genus Gossypium sp. known as gossypine A and gossypine B.

The gossypines A and B are characterized in the following manner:

The gossypines A and B are polysaccharides of molecular weight in the range $2 \times 10^4 - 10^5$ daltons.

Gossypine A corresponds to the molecular mass fraction lying between $2 \times 10^4$ and $5 \times 10^4$ daltons and contains 3.40% ± 0.3 of N and 1.32% ± 0.3 of S.

On acid hydrolysis gossypine A gives rise to monosaccharides which are converted into alditols by reduction with sodium borohydride. These reduced monosaccharides are acetylated and analyzed by the method of gas chromatography (GC) coupled to mass spectrometry (MS). Gossypine A gives rise to the results (in analyses by GC-MS) expressed as percentages of monosaccharides:

| Rha(*) | Ara | Xyl | Man | Gal | Glu | acetylated derivative |
|---|---|---|---|---|---|---|
| 1.1% | 5.7% | 1.5% | 7.6% | 40.6% | 41.8% | 1.7% |

(*) by convention the symbols Rha, Ara, Xyl, Man, Gal, Glu represent the reduced and acetylated derivatives of the corresponding sugars: rhamnose, arabinose, xylose, mannose, galactose, glucose.

Gas chromatography is carried out under the following conditions:

Glass capillary column 25 m long, 0.32 m/m in diameter, film thickness: 0.2 um; phase: Silar 10 C, column temperature: 220° C., injector temperature; 220° C., interface temperature: 250° C., helium pressure: 0.7 bar.

Mass spectrometry performed at 70 eV-0.25 uA, photomultiplier 1 300 eV.

Gossypine B corresponds to the molecular mass fraction lying between $5 \times 10^4$ and $10^5$ daltons and contains 6.7% ± 0.3 of N and 1.32% ± 0.3 of S.

On acid hydrolysis gossypine B gives rise to monosaccharides which are analyzed in the form of alditol derivatives under the same conditions as in the case of gossypine A.

The following percentages of monosaccharides are found in gossypine B by analysis on GC-MS:

| Rha | Ara | Xyl | Man | Gal | Glu | acetylated derivative |
|---|---|---|---|---|---|---|
| 3.1% | 16.3% | 6.1% | 2.5% | 33.9% | 33.3% | 4.8% |

The present invention also relates to extracts and to galactagogue active fractions extracted from the genus *Euphorbia Hirta* Linee, named EUPHORBINE A and EUPHORBINE B.

The euphorbines A and B are characterized in the following manner:

The euphorbines A and B are polysaccharides of molecular mass lying between $3 \times 10^4$ and $10^5$ daltons.

Euphorbine A corresponds to the molecular mass fraction lying between $3 \times 10^4$ and $5 \times 10^4$ daltons and contains 3.10%±0.3 of N and 1.09%±0.3 of S.

On acid hydrolysis euphorbine A gives rise to monosaccharides which are converted to the reduced form of the sugars. These reduced monosaccharides are acetylated and analyzed by the method of gas chromatography coupled to mass spectrometry (GC-MS).

On GC-MS under the same conditions as in the case of the gossypines A and B, euphorbine A gives the following results:

| Rha | Ara | Xyl | Man | Gal | Glu | acetylated derivative |
|---|---|---|---|---|---|---|
| 8.4 | 19.5% | 4.2% | 3.8% | 19.3% | 42.6% | 2.2% |

Euphorbine B is a galactagogue polysaccharide fraction of molecular mass lying between $5 \times 10^4$ and $10^5$ daltons and contains 2.5%±0.3 of N and 1.1±0.3 of S.

On acid hydrolysis euphorbine B give rise to monosaccharides which are converted into the reduced form of the sugars or alditols. The alditols obtained are acetylated and analyzed by the (GC-MS) procedure.

Euphorbine B gives the following results:

| Rha | Ara | Xyl | Man | Gal | Glu | acetylated derivative |
|---|---|---|---|---|---|---|
| 12.7% | 25.1% | 9.5% | 9.2% | 15.8% | 19.2% | 8.4% |

The products according to the present invention are of particular interest for increasing the level of plasma prolactin in humans and animals. In mammals, they increase the level of beta-casein in the mammary gland.

It is possible to take advantage of these galactagogue properties in the nursing of infants and the rearing of animals, both in the form of a medicine and in the form of a food additive.

The examples given below demonstrate other properties and advantages of the present invention.

EXAMPLE 1

To 1000 g of powdered whole plants of *Euphorbia Hirta* are added 6 liters of water. The mixture is heated at 90°–95° C. for 20 minutes. It is filtered and the solid residue is treated two more times in the same manner. The aqueous filtrates are combined and concentrated to 2 liters. This aqueous extract is lyophilized. The lyophilizate obtained is treated with refluxing ethanol for 5 minutes (3 times 500 ml). The insoluble portion weighs 98.1 g and constitutes the total polysaccharide extract.

EXAMPLE 2

To 1000 g of powdered whole plants of *Euphorbia Hirta* are added 6 liters of water and the mixture is heated at 90°–95° C. for 20 minutes. It is filtered and the solid residue is treated two more times in the same manner. The aqueous filtrates are combined and concentrated to 0.3 liter. 2 liters of ethanol are added and the precipitate is separated. The dried precipitate weighs 101.5 g and constitutes the total polysaccharide extract.

EXAMPLE 3

100 g of the total polysaccharide extract of *Euphorbia Hirta* are dissolved in 2 liters of water. The solution is filtered and the filtrate is then filtered through a selectively permeable membrane with a nominal cut-off threshold at a molecular weight of $3 \times 10^4$ daltons. The aqueous phase containing the products of molecular mass lower than $3 \times 10^4$ daltons is lyophilized to give 21.4 g. The aqueous phase containing molecules of molecular mass higher than $3 \times 10^4$ daltons is ultrafiltered through a membrane with a cut-off threshold of $10^5$ daltons. The aqueous phase containing molecules of molecular mass lying between $3 \times 10^4$ daltons and $10^5$ daltons is then ultrafiltered through a membrane with a cut-off threshold of $5 \times 10^4$ daltons. After lyophilization or nebulization of these fractions 8.3 g of euphorbine A and 2.2 g of euphorbine B are obtained.

EXAMPLE 4

To 10 kg of seed powder of Gossypium sp. are added 100 liters of water. The mixture is heated at 90°–95° C. for 20 minutes. It is filtered. The solid residue is treated two more times with 70 liters of water each time at 90°–95° C. for 20 minutes. The combined filtrates yield 2.12 kg of nebulized powder of crude polysaccharides.

EXAMPLE 5

To 100 g of nebulized powder of crude polysaccharides of Gossypium sp. are added 500 ml of ethanol and the mixture is refluxed for 5 minutes. The residue is treated two more times with ethanol (2×250 ml). The residue insoluble in ethanol (83.3 g) constitutes the total polysaccharide extract.

EXAMPLE 6

To 10 kg of seed cake of Gossypium sp. are added 100 liters of water. The mixture is heated at 90°–95° C. for 20 minutes. It is filtered and the residue is treated two more times with 70 liters of water each time at 90°–95° C. for 20 minutes. The combined filtrates yield 1.91 g of nebulized powder of crude polysaccharides.

EXAMPLE 7

To 100 g of nebulized powder of crude polysaccharides of Gossypium sp. of example 6 are added 500 ml of ethanol and the mixture is refluxed for 5 minutes. The solid residue is treated two more times with ethanol (2×250 ml). The residue insoluble in ethanol constitutes the total polysaccharide extract (90.1 g).

EXAMPLE 8

20 g of the total polysaccharide extract of Gossypium sp. of example 7 are dissolved in 5 liters of water. The aqueous solution is ultrafiltered through a membrane with a cut-off threshold of $10^5$ daltons. The fraction of molecular mass lower than $10^5$ daltons is then ultrafiltered through a membrane with a cut-off threshold of $5 \times 10^4$ daltons.

The fraction of molecular mass lower than $5 \times 10^4$ daltons is ultrafiltered through a membrane with a cut-off threshold of $2 \times 10^4$ daltons. These different aqueous fractions are lyophilized and thus yield 295 mg of gossypine A of molecular mass lying between $2 \times 10^4$ and $5 \times 10^4$ daltons and 208 mg of gossypine B of molecular mass lying between $5 \times 10^4$ and $10^5$ daltons.

EXAMPLE 9

Pharmacological Studies

Galactagogue Activity

Principle

The administration of a galactagogue to animals is expressed by:

1) an increase in the level of beta-casein in the mammary gland;
2) an increase in the level of plasma prolactin.

Radio-Immunological Assay of Beta-Casein

Three-months old female rats are distributed in groups of four animals. The product to be studied, either in suspension or in solution in 1 ml of water, is administered by gavage twice a day for 4 days. On the 5th day the mammary glands of the sacrificed animals are removed for the radio-immunological assay of beta-casein (according to the method of F. C. GREENWOOD, W. M. HUNTER AND J. G. GLOVER, Bioch. J. (1963) 89, 114). Water is administered to control female rats. The ratio of the amount of beta-casein produced in the mammary glands of treated rats to that produced in the glands of control rats is evaluated.

The results obtained are as follows:

| Dose/day | Products | Beta-casein in treated rats / Beta-casein in control rats |
| --- | --- | --- |
|  | water (control) | 1 |
| 400 mg | product of example 4 | 3 |
| 400 mg | product of example 5 | 4 |
| 400 mg | product of example 6 | 3 |
| 400 mg | product of example 7 | 4 |
| 200 mg | product of example 1 | 2 |
| 10 mg | gossypine A | 4 |
| 10 mg | gossypine B | 5 |
| 10 mg | euphorbine A | 2 |
| 10 mg | euphorbine B | 4 |

Radio-Immunological Assay of Prolactin

The level of plasma prolactin is assayed in ewes which have received the products under study by intravenous injection, using physiological serum as excipient. Blood samples are taken every 10 minutes over a period of 1 hour. The plasma obtained by centrifugation is used for the radio-immunological assay of prolactin which is expressed in ng per ml of serum. The ewes serve as their own controls. The level of plasma prolactin is assayed before and after the injection of the products under study. The results, expressed as the ratio between the maximum level of prolactin measured after injection and the base level before injection, are as follows:

| Dose/day | Products | Prolactin |
| --- | --- | --- |
|  | physiological serum (control) | 1 |
| 500 mg | product of example 4 | 4 |
| 300 mg | product of example 1 | 4 |
| 100 mg | gossypine A | 2 |
| 100 mg | gossypine B | 5 |
| 200 mg | euphorbine A | 4 |
| 50 mg | euphorbine B | 5 |

I claim:

1. A polysaccharide derived from a species of Gossypium containing monomeric units of rhamnose, arabinose, xylose, mannose, galatose, and glucose, having a molecular mass between 10,000 and 1,000,000 daltons; having 1 to 8% nitrogen and 0.8 to 2% sulfur; being substantially insoluble in ethanol; wherein said polysaccharide is selected from the group consisting of gossypine A, which has a molecular mass between 20,000 and 50,000 daltons and contains about $3.40\% \pm 0.3$ by weight of nitrogen and $1.32\% \pm 0.3$ by weight of sulfur, and gossypine B, which has a molecular mass of between 54,000 and 100,000 daltons and contains about $6.7\% \pm 0.3$ by weight of nitrogen and $1.32\% \pm 0.3$ weight of sulfur.

2. The polysaccharide of claim 1 in the form of a dry solid.

3. A composition for the enhancement of the secretion of prolactin in human or animal female mammals comprising an amount of the polysaccharide of claim 1 effective for the enhancement of said prolactin secretion combined with at least one diluent selected from the group consisting of pharmaceutically acceptable excipients and comestible materials.

* * * * *